United States Patent
Schnitman et al.

(10) Patent No.: US 9,770,570 B2
(45) Date of Patent: Sep. 26, 2017

(54) APPARATUS AND METHOD FOR MONITORING NITRIC OXIDE DELIVERY

(71) Applicant: INO Therapeutics LLC, Hampton, NJ (US)

(72) Inventors: Robert Schnitman, Colchester, CT (US); Joseph J. Medicis, Syracuse, NY (US); Jim Potenziano, Binghamton, NY (US); Jaron Acker, Madison, WI (US); Jeffrey Schmidt, Oregon, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 1273 days.

(21) Appl. No.: 13/671,057

(22) Filed: Nov. 7, 2012

(65) Prior Publication Data

US 2013/0118486 A1 May 16, 2013

Related U.S. Application Data

(60) Provisional application No. 61/556,525, filed on Nov. 7, 2011.

(51) Int. Cl.
 *A61M 16/12* (2006.01)
 *A61M 16/00* (2006.01)
 (Continued)

(52) U.S. Cl.
 CPC ...... *A61M 16/104* (2013.01); *A61M 16/0051* (2013.01); *A61M 16/0057* (2013.01);
 (Continued)

(58) Field of Classification Search
 CPC ... A61K 33/00; A61K 9/007; A61M 16/0051; A61M 16/0057; A61M 16/04; A61M 16/0666; A61M 16/0875; A61M 16/12; A61M 16/20; A61M 16/204; A61M 2016/0021; A61M 2016/0039; A61M 2016/102; A61M 2016/1025;
 (Continued)

(56) References Cited

U.S. PATENT DOCUMENTS

| | | | |
|---|---|---|---|
| 5,558,083 A | | 9/1996 | Bathe et al. |
| 5,732,693 A | * | 3/1998 | Bathe .................. A61M 16/12 128/203.12 |

(Continued)

FOREIGN PATENT DOCUMENTS

JP   2001-521416   11/2001

OTHER PUBLICATIONS

Final Office Action in U.S. Appl. No. 13/800,287, dated Aug. 11, 2015, 13 pages.
(Continued)

*Primary Examiner* — Annette Dixon

(57) ABSTRACT

Described is an apparatus for monitoring nitric oxide delivery, wherein such apparatus comprises an indicator to inform a user of the apparatus when the flow of breathing gas rises above or falls below a predetermined level or range. Also described is a method of monitoring nitric oxide delivery, wherein the flow of breathing gas is measured and displayed. In some embodiments, an alert is provided when the flow of breathing gas rises above or falls below a predetermined level or range.

9 Claims, 5 Drawing Sheets

(51) Int. Cl.
*A61M 16/10* (2006.01)
*A61M 16/06* (2006.01)
*A61M 16/08* (2006.01)

(52) U.S. Cl.
CPC ......... *A61M 16/12* (2013.01); *A61M 16/0666* (2013.01); *A61M 16/085* (2014.02); *A61M 2016/0039* (2013.01); *A61M 2016/102* (2013.01); *A61M 2202/0275* (2013.01); *A61M 2205/18* (2013.01); *A61M 2205/3334* (2013.01); *A61M 2205/502* (2013.01); *A61M 2205/581* (2013.01); *A61M 2205/583* (2013.01); *F04C 2270/041* (2013.01)

(58) Field of Classification Search
CPC .. A61M 2202/0233; A61M 2202/0275; A61M 2205/505
USPC ............ 128/203.12, 203.14, 203.24, 203.25, 128/204.18, 204.21, 204.23
See application file for complete search history.

(56) References Cited

U.S. PATENT DOCUMENTS

| | | | |
|---|---|---|---|
| 5,752,504 A | 5/1998 | Bathe | |
| 5,881,723 A | 3/1999 | Wallace et al. | |
| 5,890,490 A | 4/1999 | Aylsworth et al. | |
| 5,918,596 A * | 7/1999 | Heinonen | A61M 16/12 128/204.21 |
| 6,089,229 A * | 7/2000 | Bathe | A61M 16/12 128/203.12 |
| 6,125,846 A | 10/2000 | Bathe et al. | |
| 6,164,276 A | 12/2000 | Bathe et al. | |
| 6,581,599 B1 * | 6/2003 | Stenzler | A61M 16/12 128/203.12 |
| 7,201,166 B2 | 4/2007 | Blaise et al. | |
| 7,455,062 B2 | 11/2008 | Roehl et al. | |
| 7,523,752 B2 * | 4/2009 | Montgomery | A61M 16/0051 128/204.18 |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,431,163 B2 | 4/2013 | Baldassarre et al. | |
| 8,573,209 B2 | 11/2013 | Bathe et al. | |
| 8,573,210 B2 | 11/2013 | Bathe et al. | |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 2005/0172966 A1 * | 8/2005 | Blaise | A61M 16/12 128/204.21 |
| 2007/0062527 A1 | 3/2007 | Montgomery et al. | |
| 2007/0181126 A1 | 8/2007 | Tolmie et al. | |
| 2009/0090363 A1 * | 4/2009 | Niland | A61M 16/1075 128/203.26 |
| 2012/0199123 A1 | 8/2012 | Stenzler et al. | |
| 2013/0192595 A1 * | 8/2013 | Tolmie | A61M 16/12 128/202.22 |

OTHER PUBLICATIONS

PCT International Preliminary Report on Patentability in PCT/US2014/025442, mailed Sep. 24, 2015, 10 pages.
INOmax DS (Delivery System): Operation Manual (800 ppm INOMAX (nitric oxide) for Inhalation), Ikaria, Inc. 2010, 112 pages.
INOvent Delivery System: Operation and Maintenance Manual (CGA Variant), Datex-Ohmeda, Inc. 2000, 180 pages.
Using the INOpulse DS Subject Guide, Ikaria, Inc. 2012, 50 pages.
INOmax Label, Nitric Oxide Gas, INO Therapeutics 2013, 2 pages.
INOmax DSIR (Delivery System): Operation Manual (800 ppm INOMAX (nitric oxide) for Inhalation), Ikaria, Inc. 2012, 136 pages.
"International Search Report and Written Opinion of PCT/US2012/063883", mailed on Feb. 18, 2013 , 12 pages.
PCT International Preliminary Report on Patentability and Written Opinion in PCT/US2012/063883, dated May 22, 2014, 8 pages.
Non-Final Office Action in U.S. Appl. No. 13/800,287, dated Mar. 23, 2015, 18 pages.
PCT International Search Report and Written Opinion in PCT/US2014/025442, mailed Jul. 16, 2014, 15 pages.

* cited by examiner

APPARATUS AND METHOD FOR MONITORING NITRIC OXIDE DELIVERY

CROSS-REFERENCE TO RELATED APPLICATIONS

This application claims the benefit under 35 U.S.C. §119(e) to U.S. Provisional Application No. 61/556,525, filed Nov. 7, 2011, the entire content of which is incorporated herein by reference in its entirety.

TECHNICAL FIELD

Embodiments of the present invention generally relate to the field of apparatuses and methods for nitric oxide delivery.

BACKGROUND

Nitric oxide (NO) is a gas that, when inhaled, acts to dilate blood vessels in the lungs, improving oxygenation of the blood and reducing pulmonary hypertension. Because of this, nitric oxide is provided in inspiratory breathing gases for patients with pulmonary hypertension.

Often, apparatuses used for nitric oxide delivery require a minimum flow of breathing gas in order to operate properly. As the flow rate of breathing gas decreases, it becomes difficult to accurately measure the breathing gas flow rate with current flow sensors and injector modules. In fact, some delivery apparatuses shut down automatically when there is not a sufficient flow of breathing gas to be measured accurately. When the supply of nitric oxide is abruptly cut off, patients may experience adverse effects such as worsening of partial pressure of oxygen in arterial blood ($PaO_2$) and increasing pulmonary artery pressure (PAP).

Variability or irregularity in the flow from a support device such as a breathing gas delivery system may produce such low flow conditions, which may then result in shutdown of the inhaled NO delivery system or other NO delivery apparatus. Additionally, current inhaled NO delivery systems and other NO platforms cannot be used with gentle ventilation as gentle ventilation often requires lower flows then conventional ventilation. This can, again, result in shutdown of the delivery apparatus with resulting rebound hypertension and oxygen desaturation, which may result in adverse events as serious as death.

Therefore, there is a need to monitor and display the flow(s) from the NO delivery system to provide safe delivery of nitric oxide.

SUMMARY OF THE INVENTION

A first aspect of the invention relates to an apparatus to deliver therapeutic gas to a patient. According to one or more embodiments, the apparatus comprises a first inlet configured to be placed in fluid communication with a therapeutic gas supply comprising nitric oxide, a second inlet configured to be placed in fluid communication with a breathing gas delivery system that provides a breathing gas to the patient, a therapeutic gas injector module adapted to be placed in communication with the therapeutic gas supply to monitor and to control the flow of therapeutic gas to the patient, an outlet in fluid communication with the first inlet and second inlet and configured to supply breathing gas and therapeutic gas to a patient, and a control circuit in communication with the therapeutic gas injector module, the control circuit including a flow sensor to monitor the flow of breathing gas from the breathing gas delivery system and an indicator to inform a user of the apparatus when the flow of breathing gas rises above or falls below a predetermined level.

In one or more embodiments of this aspect, the control circuit includes a CPU and a flow controller, wherein the CPU sends and receives signals to the flow sensor and the flow controller such that the control circuit maintains a minimum flow of therapeutic gas to the patient. In certain embodiments, the control circuit further comprises clinical decision support software. In a particular embodiment, the clinical decision support software comprises instructions to reset any upper and lower limits of maximum and minimum dose to avert shutdown of the apparatus.

In certain embodiments, the indicator provides an alert when the flow of breathing gas rises above or falls below a predetermined level. According to one or more embodiments, the alert includes one or more of an audible alert, a visual alert and a text alert.

One or more embodiments of this aspect provide that the apparatus further comprises a display that provides a visual and/or numeric indication of the volumetric flow of breathing gas. In certain embodiments, the visual and/or numeric indication includes one or more of volumetric flow rate, tidal volume, and minute ventilation.

According to one or more embodiments, the breathing gas delivery system comprises a ventilation apparatus.

Certain embodiments provide that the therapeutic gas injector module comprises a neo-injector module. In a particular embodiment, the neo-injector module and flow sensor are adapted to determine flow of breathing gas as low as 0.25 L/min.

Another aspect of the invention relates to a method of monitoring the delivery of therapeutic gas to a patient comprising providing a flow of breathing gas, providing a flow of therapeutic gas comprising nitric oxide, delivering the breathing gas and therapeutic gas to a patient, measuring the flow of breathing gas to obtain a measured flow of breathing gas, and displaying the measured flow of breathing gas on a display module.

According to one or more embodiments, the method further comprises comparing the measured flow of breathing gas to a predetermined flow limit and providing an alert if the measured flow of breathing gas is above or below the flow limit. In certain embodiments, the alert includes one or more of an audible alert, a visual alert and a text alert.

In some embodiments, the predetermined flow limit comprises a low flow limit. In a particular embodiment, the low flow limit is equal to or less than 0.25 L/min. In other embodiments, the predetermined flow limit comprises a high flow limit.

In certain embodiments, the method further comprises adjusting the flow of breathing gas delivered to the patient in response to the alert.

In one or more embodiments, displaying the measured flow of breathing gas includes displaying one or more of volumetric flow rate, tidal volume, and minute ventilation.

According to certain embodiments, the display module is in communication with a nitric oxide delivery neo-injector module. In one or more embodiments with a neo-injector module, the predetermined flow limit comprises a low flow limit. In certain embodiments, the low flow limit is equal to or less than 0.25 L/min.

One or more embodiments provide that the method further comprises drawing a volume of combined breathing gas and therapeutic gas less than or equal to 100 mL/min and measuring one or more of the nitric oxide concentration, nitrogen dioxide concentration, and oxygen concentration of the volume of gas. In a particular embodiment, the volume of gas drawn is less than or equal to 50 mL/min.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Certain embodiments of the invention generally provide an apparatus for delivering a therapeutic gas comprising nitric oxide to a patient. The therapeutic gas comprises nitric oxide in a carrier gas such nitrogen. Suitable therapeutic gases can have varying concentrations of nitric oxide, and exemplary concentrations of nitric oxide in the therapeutic gas are 100 ppm to 10,000 ppm. In a particular embodiment, the concentration of nitric oxide is about 800 ppm.

The apparatus includes a therapeutic gas injector module that is in communication with a control circuit which informs a user when flow of a breathing gas rises above a certain level or range or falls below another level or range. Other embodiments pertain to a method of monitoring the delivery of therapeutic gas comprising nitric oxide to a patient.

In one aspect, provided are apparatuses that comprise: a first inlet for receiving a therapeutic gas supply comprising nitric oxide; a second inlet for receiving a breathing gas; a therapeutic gas injector module in communication with the therapeutic gas supply to monitor and to control the flow of therapeutic gas to a patient; an outlet in fluid communication with the first inlet and second inlet for supplying breathing gas and therapeutic gas to a patient; and a control circuit in communication with the therapeutic gas injector module for triggering an indication or warning when the flow of the breathing gas is outside of a desired range.

Figure 1:
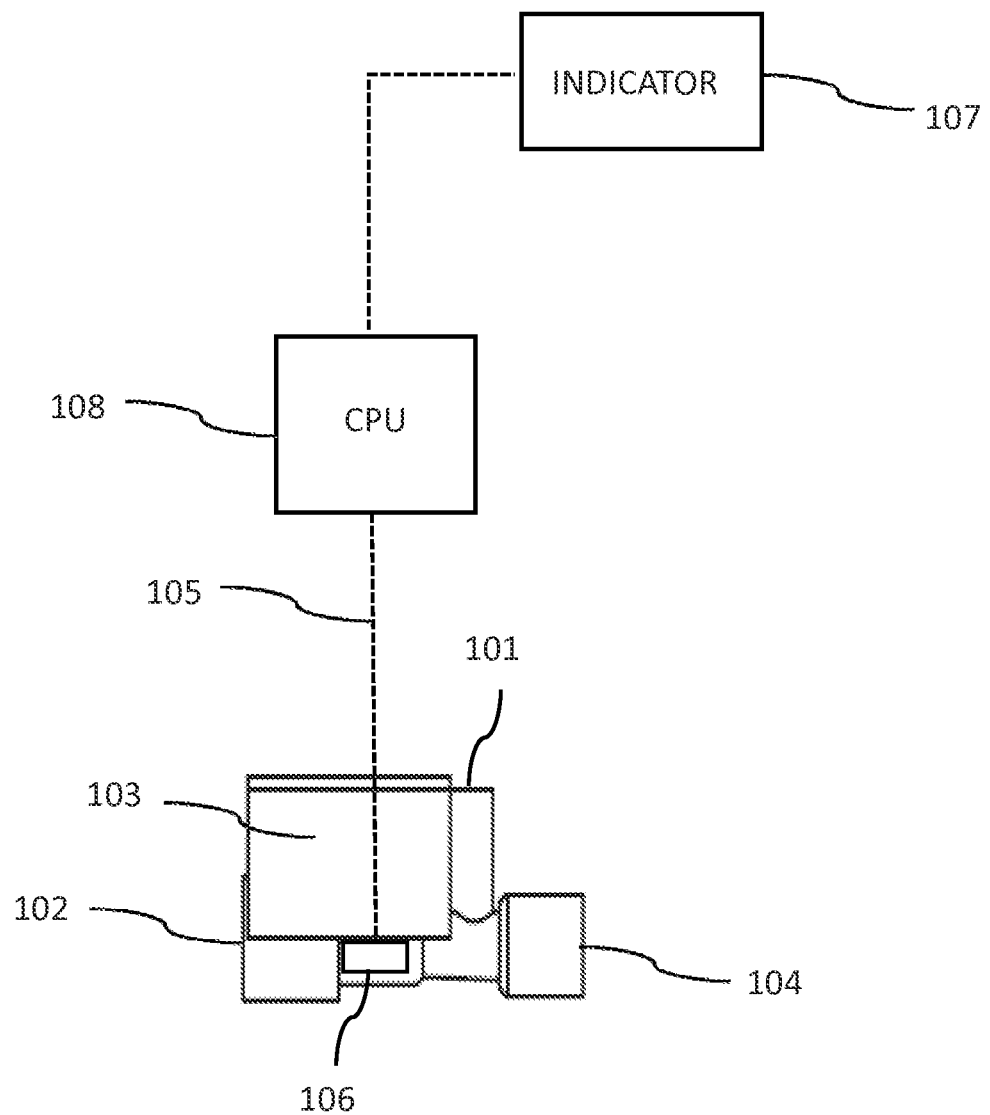
FIG. 1 depicts an apparatus for monitoring delivery of a therapeutic gas to a patient in accordance with one or more embodiments of the invention.

One or more embodiments relate to an apparatus comprising: a first inlet configured to be placed in fluid communication with a therapeutic gas supply comprising nitric oxide; a second inlet configured to be placed in fluid communication with a breathing gas delivery system that provides a breathing gas to the patient; a therapeutic gas injector module adapted to be placed in communication with the therapeutic gas supply to monitor and to control the flow of therapeutic gas to the patient; an outlet in fluid communication with the first inlet and second inlet and configured to supply breathing gas and therapeutic gas to a patient; and a control circuit in communication with the therapeutic gas injector module, the control circuit including a flow sensor to monitor the flow of breathing gas from the breathing gas delivery system and an indicator to inform a user of the apparatus when the flow of breathing gas rises above or falls below a predetermined level FIG. 1 illustrates one embodiment of an apparatus for monitoring delivery of a therapeutic gas in accordance with this aspect. First inlet 101 is configured to be placed in fluid communication with a therapeutic gas comprising nitric oxide. Second inlet 102 is configured to be placed in fluid communication with a breathing gas delivery system that provides a breathing gas to a patient. Therapeutic injector module 103 is in fluid communication with first inlet 101 and second inlet 102, as well as outlet 104. The side view of therapeutic injector module 103 is shown. Outlet 104 is in fluid communication with first inlet 101 and second inlet 102, and is configured to supply breathing gas and therapeutic gas to a patient. Flow sensor 106 is in fluid communication and downstream of second inlet 102, and monitors the flow of breathing gas through therapeutic injector module 103. Control circuit 105 is in communication with therapeutic injector module 103, and connects flow sensor 106 to CPU 108 and indicator 107. When the flow rate as measured by flow sensor 106 is above or below a predetermined level, central processing unit (CPU) 108 sends a signal to indicator 107. Indicator 107 can inform a user of the apparatus that the flow is outside of a particular range. The indicator 107 may be part of a display, such as an icon or graphic on a display screen.

The flow sensor 106 can be any appropriate flow measuring device. This includes, but is not limited to, a pneumotach, hot wire anemometer, thermal flow sensor, variable orifice, thermal time-of-flight, rotating vane and the like. Also suitable are flow transducers that measure pressure, such as a pressure drop though an orifice, in order to determine flow. According to one embodiment, the flow sensor 106 is part of the therapeutic injector module 103. In one such embodiment, the flow sensor 106 comprises a hot film sensor and a thermistor. The thermistor measures the temperature of the breathing gas flowing through the injector module 103. The hot film sensor measures the flow of breathing gas, using the temperature as measured by the thermistor. In other embodiments, the flow sensor 106 is upstream of the therapeutic injector module 103.

The term "control circuit" is intended to encompass a variety of ways that may be utilized to carry out various signal processing functions to operate the therapeutic gas delivery apparatus. In a particular embodiment, the control circuit includes a CPU 108 and a flow controller. The CPU 108 can send and receive signals to the flow sensor 106 and the flow controller (not shown) such that the control circuit maintains a minimum flow of therapeutic gas to the patient. In a specific embodiment, the CPU obtains information from the flow sensor and from an input device that allows the user to select the desired dose of nitric oxide.

In a specific embodiment of a control circuit, the flow sensor 106 is in communication with a CPU 108 that monitors the flow of each of the gases to patient as described herein. If a specific dose of nitric oxide is to be administered, the CPU 108 can calculate the necessary flow of therapeutic gas based on the measured flow of breathing gas and the concentration of nitric oxide in the therapeutic gas. Such a calculation can be performed using the following equation:

$$Q_{therapeutic} = [\gamma_{set}/(\gamma_{therapeutic} - \gamma_{set})] * Q_{breathing}$$

wherein $Q_{breathing}$ is the flow rate of breathing gas, $\gamma_{set}$ is the desired nitric oxide concentration, $\gamma_{therapeutic}$ is the concentration of nitric oxide in the therapeutic gas supply, and $Q_{therapeutic}$ is the necessary flow of therapeutic gas to provide the desired concentration of nitric oxide in the gas mixture.

The central processing unit may be one of any forms of a computer processor that can be used in an industrial or medical setting for controlling various medical gas flow devices and sub-processors. The CPU can be coupled to a memory (not shown) and may be one or more of readily available memory such as random access memory (RAM), read only memory (ROM), flash memory, compact disc, floppy disk, hard disk, or any other form of local or remote digital storage. Support circuits (not shown) can be coupled to the CPU to support the CPU in a conventional manner. These circuits include cache, power supplies, clock circuits, input/output circuitry, subsystems, and the like.

The control circuit may further comprise clinical decision support software. Such software may provide instructions for a variety of tasks, such as providing alerts when the measured flow of breathing gas rises above or falls below a predetermined level. The predetermined level may be the level at which the apparatus shuts down. Alternatively, the predetermined level may be a level that is reached prior to apparatus shutdown. Thus, for an apparatus that shuts down when the flow drops below a minimum threshold, the predetermined level may be above this minimum threshold.

The predetermined level may be built into the clinical decision support software, or it may be provided by the user through an input device. In one embodiment, the clinical decision support software comprises instructions to reset the upper and lower limits of maximum and minimum concentrations or flows at which a shutdown is triggered. According to certain embodiments, the clinical decision software comprises instructions to provide an alert when these limits are reached and avert the potential for shutdown of the apparatus, which would lead to the lack of drug delivery. Alternatively, the apparatus may comprise clinical decision software that provides instructions such that the apparatus may automatically adjust these limits without the need for user intervention.

The clinical decision software may also include instructions to alter the time sensitivity of the apparatus to changes in breathing gas flow. As a result, the apparatus may change the time period necessary for a sustained low flow condition before the apparatus shuts down. For example, the apparatus can increase the time before shutdown from about 1 to 2 seconds to several seconds, so that a shutdown will only occur if the low flow is sustained for a longer period of time.

The apparatus also comprises an indicator to inform a user of the apparatus when the flow of breathing gas rises above or falls below a predetermined level. In one or more embodiments, the indicator provides an alert when the flow of breathing gas rises above or falls below the predetermined level. In certain embodiments, the alert includes one or more of an audible alert, a visual alert and a text alert. Such alerts can be provided at the location of the apparatus itself, or may be provided at a remote location, such as directly to the medical staff or to a nursing station. When the alert is provided to a remote location, the signal may be transferred from the apparatus to the remote location by any wired or wireless communication. Examples of alerts include text messages, sirens, sounds, alarms, flashing images, changes in display color, or any other means of attracting the attention of a user.

In certain embodiments, more than one alert may be provided. For example, a low priority alert may be provided when the flow of breathing gas falls below a first predetermined level, and a high priority alert may be provided when the flow of breathing gas falls below a second, lower predetermined level. Such a tiered alert system can put medical staff on notice of a relatively small deviation in flow rate, but also provide a more serious alert when a dangerous condition exists that requires immediate attention. Alternatively, a high priority alert can be provided when the flow rate is below the predetermined level for a certain period of time, thus indicating a sustained low flow condition.

The apparatus can also include a display that provides a visual and/or numeric indication of the volumetric flow of breathing gas. This visual and/or numeric indication can include any means of displaying the flow of breathing gas, including numerals, graphics, images or the like. The display can also be any sort of appropriate display device, including a dial, gauge or other analog device, or any electronic display device, including an LED, LCD, CRT, etc. Such device need not necessarily be connected to the apparatus and may be utilized in a remote capacity. In certain embodiments, the visual and/or numeric indication includes one or more of volumetric flow rate, tidal volume, and minute ventilation. The displayed flow rate may include one or more of the following: average flow rate, instantaneous flow rate, peak flow rate, minimum measured flow rate, or other like measurements relating to the breathing gas flow.

Figure 5:
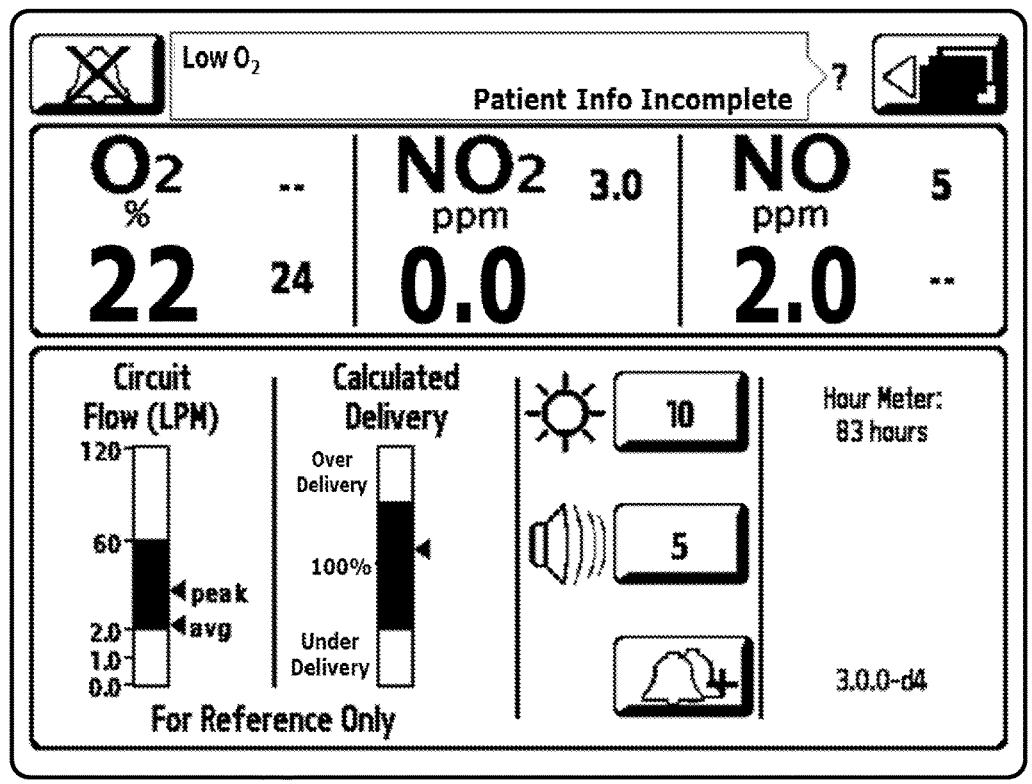
FIG. 5 depicts a screen displaying the flow of breathing gas in accordance with one or more embodiments of the invention.

An exemplary screen displaying the flow of breathing gas is shown in FIG. 5. The screen in FIG. 5 has an indicator in the bottom left corner showing the average and peak flow rates of breathing gas. In FIG. 5, the indicator has a range of 0.0 to 120 standard liters per minute. The black region from 2.0 to 60 liters per minute is the target range for the breathing gas, with 60 liters per minute as a high flow limit and 2.0 liters per minute as a low flow limit. The white regions above 60 liters per minute and below 2.0 liters per minute may be regions where delivery accuracy may differ from the published specification, or where which an alarm is emitted or other notification is given to the user such that the user is informed to make an appropriate correction to the respiratory device or the iNO delivery system. The low flow and high flow limits may be adjusted depending on the sensitivity of the flow sensor and/or injector module, or depending on the patient to be treated. As can be seen from FIG. 5, the screen may also display other information, such as the $O_2$, $NO_2$ and NO concentrations that are administered to the patient. In addition, the screen shown in FIG. 5 may also display other parameters relating to the breathing gas flow and nitric oxide delivery, such as the instantaneous breathing gas flow rate, minimum measured breathing gas flow rate, average nitric oxide flow rate, instantaneous nitric oxide flow rate, minimum and maximum nitric oxide flow rates, target nitric oxide delivery concentration, cylinder nitric oxide concentration, etc.

The CPU may also calculate a delivery concentration based on the measured nitric oxide flow rate and the measured flow rate through the breathing circuit. The calculated delivery concentration may be compared to the delivery concentration set by the user to provide a calculated delivery expressed as a percentage, with 100% being ideal delivery. This calculated delivery may also be displayed on the screen as shown in FIG. 5. In FIG. 5, the calculated delivery indicator has a black target delivery region, a white over delivery region and a white under delivery region. The target delivery region may be based on a certain accuracy tolerance for nitric oxide delivery, such as +/−1%, +/−2%, +/−5%, +/−10%, +/−15%, +/−20%, +/−25%, +/−30%, +/−35%, +/−40%, +/−45% or +/−50%. If the calculated delivery is in the white over delivery region or the white under delivery region, an alarm may be emitted or other notification may be provided to the user. As with the displayed flow of breathing gas, the calculated delivery may be displayed as an instantaneous value, average value, minimum value and/or maximum value.

In some embodiments, the flow rate of breathing gas is displayed on the main screen used during therapy. However, in one or more alternate embodiments, the flow rate is not directly displayed on the main screen, but the user may access a screen that displays information such as the breathing flow rate history or the instantaneous breathing gas flow rate. The breathing flow rate history may include the peak and/or average flow rates for a certain period of time, such as the past 5, 10, 15, 20, 30 or 45 seconds, the past 1, 2, 5, 10, 15, 20, 30, 45, 60 minutes, or since the start of the current therapy administration. In some embodiments, the breathing flow rate history is provided for the past several seconds, such as about 10 seconds. The apparatus may include appropriate components for calculating and storing the information regarding breathing flow rate history, such as a CPU and memory.

The apparatus may comprise an input device that can receive input from a user. Such user input can include operation parameters, such as desired nitric oxide concentration and flow limits. In one embodiment, an input device and display device may be incorporated into one unit, such as a touchscreen device.

The breathing gas delivery system can include any system capable of providing a supply of breathing gas to the patient. The breathing gas may be supplied by ventilatory support, mechanically assisted ventilation or by spontaneous ventilation. Examples of suitable ventilation apparatuses include, but are not limited to, conventional ventilators, jet ventilators, high frequency oscillator ventilators and continuous positive airway pressure (CPAP) apparatuses. Non-invasive approaches can also be used to supply the breathing gas, including bubble CPAP, synchronized inspiratory positive airway pressure (SiPAP), nasal cannula and heated high flow nasal cannula.

The therapeutic injector module combines the flow of the breathing gas and the flow of the therapeutic gas. The injector module ensures the proper delivery of inhaled nitric oxide at a set dose based on changes in flow of the breathing gas via communication with the CPU. In some embodiments, the therapeutic injector module is a conventional injector module. However, conventional delivery systems and injector modules are often incapable of determining flow rates below 2 L/min. Thus, according to certain embodiments, the therapeutic gas injector module comprises a neo-injector module. As used herein, a neo-injector module describes an injector module capable of determining low flow rates of breathing gas.

In certain embodiments, the neo-injector module is an injector module capable of determining flow rates below 2 L/min. According to one or more embodiments, the neo-injector module can determine flow rates as low as 0.5 L/min to 0.05 L/min. In other embodiments, the neo-injector module can determine flow rates as low as 0.25 L/min. In other embodiments, the neo-injector module is capable of determining flow rates as low as 0.125 L/min. Other embodiments provide a neo-injector module capable of determining flow rates as low as 0.05 L/min.

Neo-injector modules will typically have smaller diameters than conventional injector modules. A typical conventional injector module has a breathing gas inlet inner diameter in the range of 20 to 25 mm, a gas outlet inner diameter in the range of 13 to 17 mm, and an internal taper with a diameter in the range of 7 to 10 mm. In contrast, according to certain embodiments, a neo-injector module has a breathing gas inlet inner diameter in the range of 14 to 20 mm, a gas outlet inner diameter in the range of 9 to 13 mm, and an internal taper with a diameter in the range of 4 to 7 mm. In certain embodiments, the neo-injector module has a breathing gas inlet inner diameter in the range of 15 to 18 mm, a gas outlet inner diameter in the range of 10 to 12 mm, and an internal taper with a diameter in the range of 5.5 to 6.5 mm.

When the apparatus comprises a neo-injector module, the apparatus can be capable of providing and/or recognizing low flow rates, i.e. below 2 L/min. Such an apparatus is suitable for use with gentle ventilation strategies. Gentle ventilation may be a ventilator strategy that limits shear stress and pressures on the alveoli, while maintaining adequate oxygenation and ventilation, to reduce lung injury and minimize long term pulmonary complications. Gentle ventilation includes, but is not limited to: (1) maintaining adequate ventilation and oxygenation of the neonate; (2) limiting peak to peak pressures during mechanical ventilation; (3) adjusting ventilator pressure(s) as needed to maintain adequate lung volume without doing harm.

In some embodiments, gentle ventilation involves reducing inspiratory pressure enough to allow for some permissive hypercapnia. Gentle ventilation may include, but is not limited to, utilization of non-invasive ventilation (NIV) methods of respiratory support to limit injury to the lung, whereby the device and equipment supplies gas flow at lower pressures, thus eliminating the breath-to-breath high PIP's (Peak Airway Pressures) which increases the frequency of lung injury through shearing forces and stretching of alveoli. Gentle ventilation may include the use of bubble CPAP, SiPAP, HHHFNC (Heated Humidified High Flow Nasal Cannula) and methods of mechanical ventilation, whereby the intubated infant receives PIP's less than or equal to 20 cm $H_2O$ and oxygen saturations are 88-92%. For those infants on HFOV or HJV, pressures are maintained to minimize lung injury. Equipment to maintain an approach to gentle ventilation includes, but is not limited to, nasal cannula, nasal prongs and adaptive masks for NIV support. Examples of suitable equipment for gentle ventilation are Neopuff® and High Flow Bubble CPAP available from Fisher & Paykel Healthcare, Inc., and products available from Vapotherm, Inc.

Another aspect of the invention relates to a system for delivering therapeutic gas to a patient. The system comprises: a therapeutic gas supply comprising nitric oxide; a breathing gas delivery system that provides breathing gas to a patient; and a therapeutic gas delivery apparatus, wherein the therapeutic gas delivery apparatus comprises: a first inlet configured to be placed in fluid communication with the therapeutic gas supply; a second inlet configured to be placed in fluid communication with the breathing gas delivery system; a therapeutic gas injector module adapted to be placed in communication with the therapeutic gas supply to monitor and to control the flow of therapeutic gas to the patient; an outlet in fluid communication with the first inlet and second inlet and configured to supply breathing gas and therapeutic gas to a patient; and a control circuit in communication with the therapeutic gas injector module, the control circuit including a flow sensor to monitor the flow of breathing gas from the breathing gas delivery system and an indicator to inform a user of the apparatus when the flow of breathing gas rises above or falls below a predetermined level.

Figure 2:
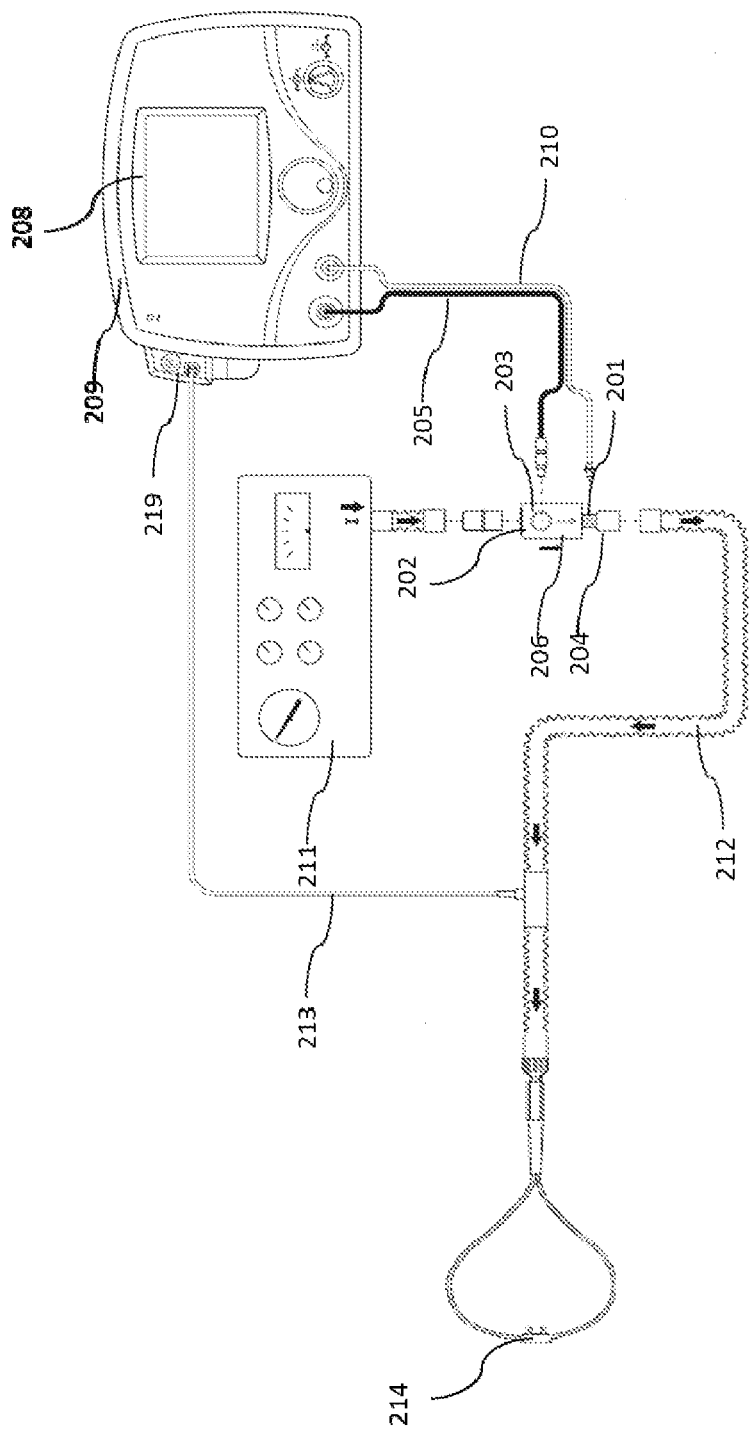
FIG. 2 depicts a system for providing a therapeutic gas to a patient in accordance with one or more embodiments of the invention.

FIG. 2 illustrates one embodiment of a system for providing a therapeutic gas to a patient in accordance with this aspect. Therapeutic injector module 203 is in fluid communication with first inlet 201 and second inlet 202. First inlet 201 is in fluid communication with therapeutic gas injector tube 210, which is in fluid communication with a therapeutic gas supply comprising nitric oxide. Second inlet 202 is in fluid communication with breathing gas delivery system 211, which is illustrated as a ventilator. The arrows in FIG. 2 indicate the direction of flow for the breathing gas and the combined gas mixture of therapeutic gas and breathing gas. Flow sensor 206 is in fluid communication and downstream of second inlet 202, and monitors the flow of breathing gas through therapeutic injector module 203. The top view of therapeutic injector module 203 is shown. The therapeutic gas and breathing gas mix in therapeutic injector module 203 to provide a gas mixture. Injector module cable 205 connects therapeutic injector module 203 with control module 209. Control module 209 comprises display 208, which can display real-time flow of breathing gas and/or provide alerts when the flow of breathing gas rises above or falls below a predetermined level. Inspiratory breathing hose 212 is in fluid communication with outlet 204 and nasal cannula 214. The inspiratory breathing hose provides the gas mixture of breathing gas and therapeutic gas to nasal cannula 214, which delivers the gas mixture to the patient. Patient gas sample line 213 diverts some of the flow of the gas mixture from inspiratory breathing hose 212 and brings it to sample block 219.

Sample block 219, also known as a sample pump, draws some of the flow of the gas mixture through gas sample line 213. As shown in FIG. 2, the sample block 219 may be incorporated into the control module 209. The sample block analyzes the concentrations of nitric oxide, oxygen, and nitrogen dioxide in the gas mixture. Typically, a sample block will sample about 250 mL/min of the gas mixture. However, when flow rates of breathing gas are near 250 mL/min, sampling 250 mL/min of the gas mixture would leave little or no gas to deliver to the patient. Therefore, in one or more embodiments, the sample block is modified to draw or pull a volume of combined therapeutic and breathing gas such that the gas sampled per minute is less than or equal to 100 mL/min. In certain embodiments, the gas sampled is less than or equal to 50 mL/min. In further embodiments, the gas sampled is less than or equal to 20 mL/min. The sampling block may have smaller pumps or more sensitive sensors in order to sample lower flow rates.

The concentrations of nitric oxide, oxygen and nitrogen dioxide measured in the sample block 219 may be shown on display 208. As a result of sampling lower amounts of the gas mixture, refresh rates of monitored values may need to be faster regarding displayed values.

The therapeutic gas delivery apparatus in the therapeutic gas delivery system can incorporate any or all of the previously described embodiments for a therapeutic gas delivery apparatus.

The breathing gas delivery system in the system for delivering therapeutic gas can include any system capable of providing a supply of breathing gas to the patient. The breathing gas may be supplied by any form of ventilatory support, or mechanically assisted ventilation or by spontaneous ventilation. Examples of suitable ventilation apparatuses include, but are not limited to, conventional ventilators, jet ventilators, high frequency oscillator ventilators and CPAP apparatuses. Non-invasive approaches can also be used to supply the breathing gas, including bubble CPAP, SiPAP, nasal cannula and heated high flow nasal cannula.

According to another aspect of the invention, provided is a method of monitoring the delivery of therapeutic gas to a patient comprising: providing a flow of breathing gas; providing a flow of therapeutic gas comprising nitric oxide; delivering the breathing gas and therapeutic gas to a patient; measuring the flow of breathing gas to obtain a measured flow of breathing gas; and displaying the measured flow of breathing gas on a display module.

Figure 3:
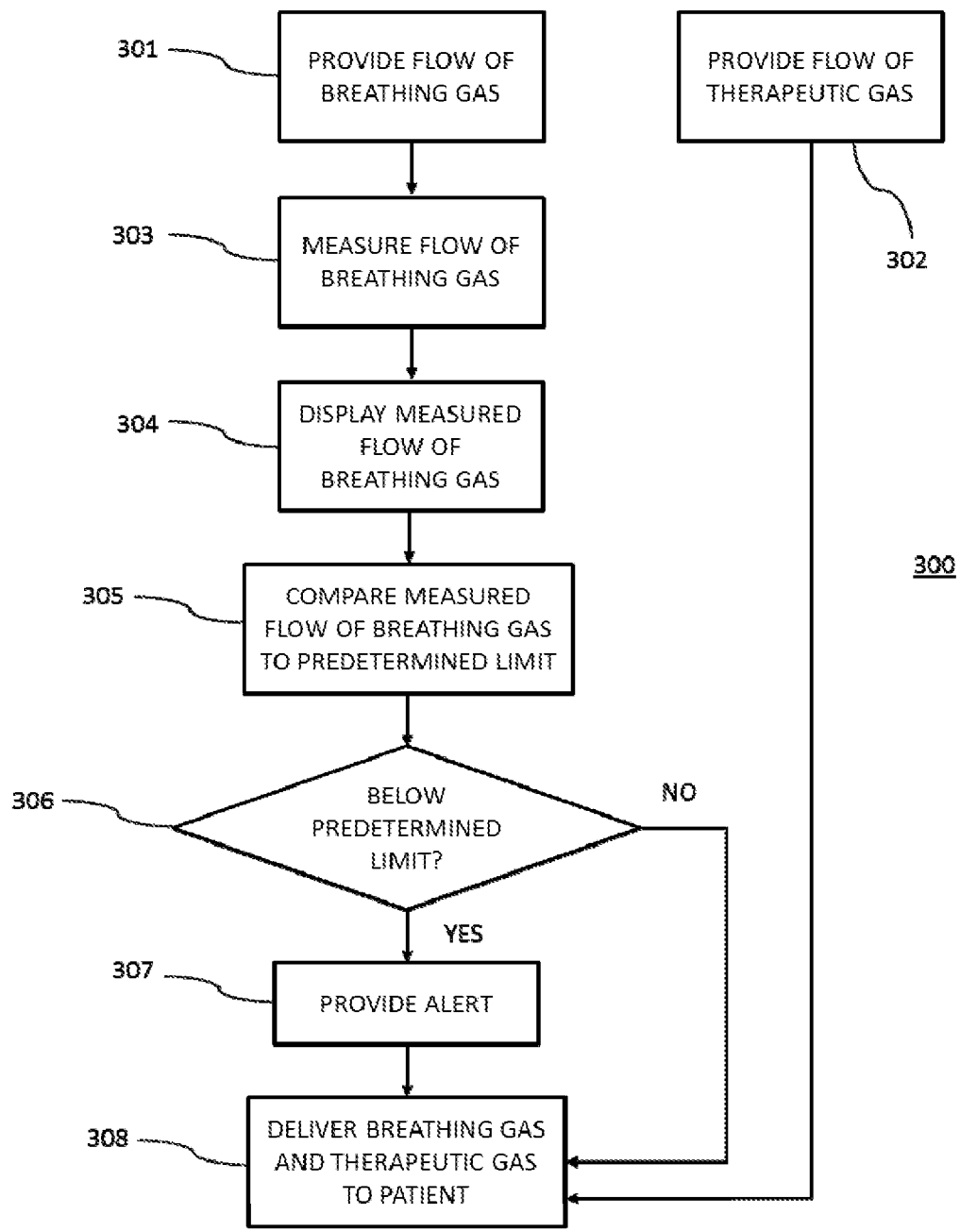
FIG. 3 depicts a flow chart for a method of monitoring the delivery of therapeutic gas to a patient in accordance with one or more embodiments of the invention.

FIG. 3 depicts a flow chart for one embodiment of a method 300 for monitoring the delivery of therapeutic gas to a patient. A flow of breathing gas is provided 301 to a delivery apparatus, such as a therapeutic injector module. A flow of therapeutic gas comprising nitric oxide is also provided 302 to the delivery apparatus. The flow of breathing gas is measured 303, and this measured flow of breathing gas is displayed 304 on a display module. Next, the measured flow of breathing gas is compared 305 to a predetermined limit. In FIG. 3, the predetermined limit is a low flow limit. If the measured flow of breathing gas is below 306 the predetermined limit, an alert is provided 307. The breathing gas and therapeutic gas are then delivered 308 to a patient. If the measured flow of breathing gas is not below 306 the predetermined limit, then the breathing gas and therapeutic gas are delivered 308 to a patient without providing 307 an alert.

Figure 4:
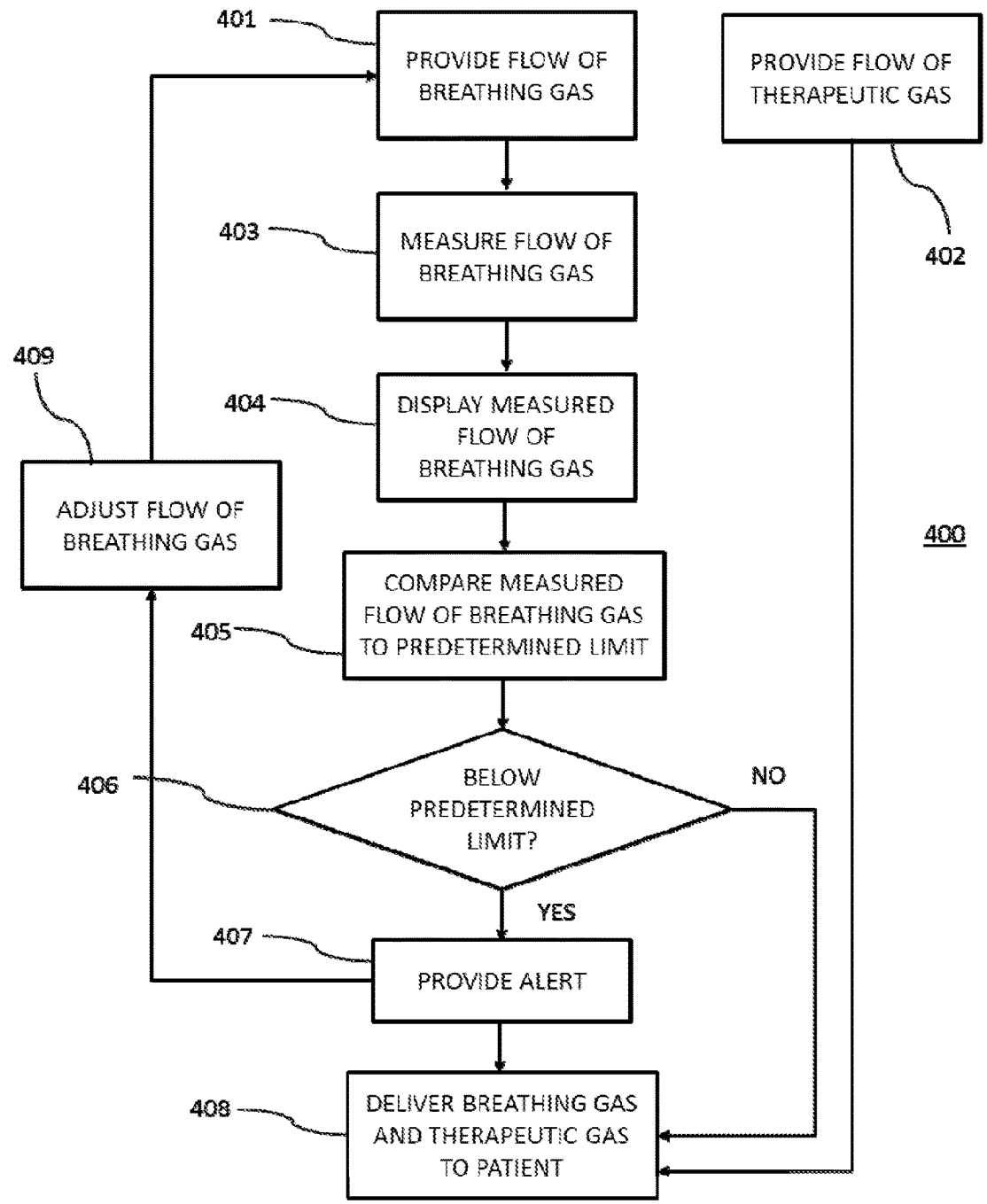
FIG. 4 depicts a flow chart for another method of monitoring the delivery of therapeutic gas with a feedback loop to drive dose or adjust flows to a patient in accordance with one or more embodiments of the invention.

FIG. 4 depicts a flow chart for another embodiment of a method 400 for monitoring the delivery of therapeutic gas to a patient. A flow of breathing gas is provided 401 to a delivery apparatus, and a flow of therapeutic gas comprising nitric oxide is also provided 402. The flow of breathing gas is measured 403, and the measured flow of breathing gas is displayed 404 on a display module. The measured flow of breathing gas is then compared 405 to a predetermined flow limit, which is a low flow limit in FIG. 4. As with FIG. 3, if the measured flow of breathing gas is below 406 the predetermined limit, an alert is provided 407. In response to the alert provided 407, the flow rate of breathing gas is adjusted 409. The breathing gas and therapeutic gas comprising nitric oxide are then delivered 408 to the patient. If the measured flow of breathing gas is not below 406 the predetermined limit, then proceed directly to delivering 408 the breathing gas and therapeutic gas comprising nitric oxide.

In certain embodiments, the method further comprises comparing the measured flow of breathing gas to a predetermined flow limit and providing an alert if the measured flow of breathing gas is above or below the flow limit. In a particular embodiment, the predetermined flow limit is a low flow limit. The low flow limit will depend on the characteristics of the apparatus used to deliver the therapeutic gas. In certain embodiments, the low flow limit is 0.25 L/min.

In another embodiment, the predetermined flow limit is a high flow limit. In certain embodiments, the high flow limit prevents overextending the patient's lungs. The high flow limit can depend on the lung volume of the patient, which is often derived from the ideal body weight of a patient. A patient's ideal body weight is a function of the patient's height and gender.

An alert may be provided when the flow of breathing gas rises above or falls below a predetermined flow limit. In certain embodiments, the alert includes one or more of an audible alert, a visual alert and a text alert. Such alerts can be provided at the location of the apparatus itself, or may be provided at a remote location, such as directly to the medical staff or to a nursing station.

In specific embodiments, the method further comprises adjusting the flow of breathing gas delivered to the patient in response to the alert. The flow can be adjusted either manually by medical staff, or it may be adjusted automatically by the apparatus. According to a certain embodiment, a CPU in communication with the breathing gas delivery system uses clinical decision software to determine when the flow of breathing gas is below or above the predetermined limit, and sends a signal to the breathing gas delivery system to adjust the breathing gas flow rate to be within the predetermined flow limit.

In one or more embodiments, displaying the measured flow of breathing gas includes displaying one or more of volumetric flow rate, tidal volume, and minute ventilation. The displaying can be any visual and/or numeric indication, including numerals, graphics, images or the like. The display module can be performed by any appropriate display device, including a dial, gauge or other analog device, or any electronic display device, including an LED, LCD, CRT, etc.

According to a particular embodiment, the display module is in communication with a nitric oxide delivery neo-injector module. In certain embodiments, the neo-injector module is capable of recognizing flow rates as low as 0.25 L/min. In other embodiments, the neo-injector module is capable of recognizing flow rates as low as 0.125 L/min.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments. The order of description of the above method should not be considered limiting, and methods may use the described operations out of order or with omissions or additions.

It is to be understood that the above description is intended to be illustrative, and not restrictive. Many other embodiments will be apparent to those of ordinary skill in the art upon reviewing the above description. The scope of the invention should, therefore, be determined with reference to the appended claims, along with the full scope of equivalents to which such claims are entitled.

What is claimed is:

1. A method of monitoring the delivery of therapeutic gas to a patient comprising:
   receiving to a gas delivery device a desired concentration of therapeutic gas;
   providing a flow of breathing gas;
   providing a flow of therapeutic gas comprising nitric oxide;
   delivering a combined flow of the breathing gas and the therapeutic gas to a patient;
   measuring via a first flow sensor a measured flow rate of the breathing gas;
   obtaining a flow rate of the therapeutic gas that is one of a measured flow rate and a known flow rate;
   determining, using the flow rate of the therapeutic gas and the flow rate of the breathing gas, a calculated delivered concentration of therapeutic gas in the combined flow; and
   presenting on a display a visual indication of the calculated delivery concentration of nitric oxide as a percentage comparison to the desired delivery concentration, wherein the visual indication includes a first region representing over delivery and a second region representing under delivery wherein the visual indicator further includes a marker associated with one of the first region and second region.

2. The method of claim 1 further comprising comparing the measured flow of breathing gas to a predetermined flow limit and providing an alert if the measured flow of breathing gas is above or below the flow limit.

3. The method of claim 2, wherein the alert includes one or more of an audible alert, a visual alert and a text alert.

4. The method of claim 2, wherein the predetermined flow limit comprises a low flow limit equal to or less than 0.25 L/min.

5. The method of claim 2, wherein the predetermined flow limit comprises a high flow limit.

6. The method of claim 2, further comprising adjusting the flow of breathing gas delivered to the patient in response to the alert.

7. The method of claim 1, further comprising presenting the measured flow of breathing gas on the display, wherein displaying the measured flow of breathing gas includes displaying one or more of volumetric flow rate, tidal volume, and minute ventilation.

8. The method of claim 1, further comprising presenting the measured flow of breathing gas on the display, wherein the measured flow of breathing gas is one or more of an average flow rate, an instantaneous flow rate, a peak flow rate and a minimum measured flow rate.

9. The method of claim 1 wherein the visual indication includes an over delivery region, an under delivery region and disposed between the over delivery region and under delivery region a target delivery region, and further includes an arrowhead indicating the delivered concentration of therapeutic gas.

* * * * *